US00PP29915P2

(12) United States Plant Patent
O'Connell

(10) Patent No.: US PP29,915 P2
(45) Date of Patent: Nov. 27, 2018

(54) ***ECHINOPSIS* PLANT NAMED 'RUBY STARLIGHT'**

(50) Latin Name: *Echinopsis hybrida*
Varietal Denomination: Ruby Starlight

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/732,288

(22) Filed: Oct. 18, 2017

(51) Int. Cl.
*A01H 5/02* (2018.01)

(52) U.S. Cl.
USPC ..... Plt./372

(58) Field of Classification Search
USPC ..... Plt./372
See application file for complete search history.

*Primary Examiner* — Annette H Para
(74) *Attorney, Agent, or Firm* — Cassandra Bright

(57) ABSTRACT

A new and distinct *Echinopsis* cultivar named 'Ruby Starlight' is disclosed, characterized by distinctive ruby red flowers in a triple whorl, occurring between March and July. Offsetting begins at an early age, producing clusters of peanuts more quickly than comparable varieties. Plants are fast growing and very free offsetting, resulting in both improved propagation rates and improved finished plant production times. *Echinopsis* is an ornamental cactus, useful as an indoor ornamental plant and outdoors in warm climates.

3 Drawing Sheets

Latin name of the genus and species: *Echinopsis hybrida*.
Variety denomination: 'RUBY STARLIGHT'.

BACKGROUND OF THE INVENTION

The new cultivar, *Echinopsis* 'Ruby Starlight', was of a planned breeding program conducted by the inventor, Renee O'Connell at a commercial greenhouse in Vista, Calif. A crossing resulting in the new variety was made during May of 2012. The seed parent is the unpatented proprietary variety *Echinopsis hybrida* 'Rose 09'. The pollen parent is the unpatented proprietary variety *Echinopsis hybrida* 'Laser Light'. *Echinopsis* 'Ruby Starlight' was selected by the inventor, Renee O Connell, in June, 2013 from a group of seedlings resulting from the 2012 crossing, at a commercial greenhouse in Vista, Calif.

Asexual reproduction of the new cultivar 'Ruby Starlight' was first performed in Vista, Calif., at a commercial greenhouse, by vegetative offsets, known as "peanuts" in July, 2013. 'Ruby Starlight' has since produced multiple generations and has shown that the unique features of this cultivar are stable and reproduced true to type.

SUMMARY OF THE INVENTION

The cultivar 'RUBY STARLIGHT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUBY STARLIGHT' These characteristics in combination distinguish 'RUBY STARLIGHT' as a new and distinct *Echinopsis* cultivar:

1 The new cultivar *Echinopsis* 'Ruby Starlight' displays unusual ruby red flowers, as compared with many other *Echinopsis* hybrids with pink, rose, orange or yellow flowers.

2. The new cultivar *Echinopsis* 'Ruby Starlight' offsets at an early age, producing clusters of "peanuts" relatively quickly as compared to many other *Echinopsis* hybrids.
3. Production times are enhanced for *Echinopsis* 'Ruby Starlight' due to the freely produced offsets, as compared to many other *Echinopsis* hybrids.
4. The new cultivar *Echinopsis* 'Ruby Starlight' displays several "flushes" of flowering, beginning in March, and continuing into July, as compared to many other *Echinopsis* that flower during a particular period, and then do not flower again until the following year.

Plants of the new cultivar 'RUBY STARLIGHT' are similar to plants of the seed parent, in most horticultural characteristics, however, plants of the new cultivar 'RUBY STARLIGHT' differ in the following;

1. The new cultivar *Echinopsis* 'Ruby Starlight' displays flowers of a clear, ruby red, whereas the seed parent *Echinopsis* 'Rose 09' produces rose colored flowers.
2. *Echinopsis* 'Ruby Starlight' produces "peanuts" with light colored areoles and relatively short reddish brown spines, whereas the spines of *Echinopsis* 'Rose 09' are more honey colored and longer.
3. The morphology of *Echinopsis* 'Ruby Starlight' is relatively short in height, whereas *Echinopsis* 'Rose 09' displays a taller morphology.
4. *Echinopsis* 'Ruby Starlight' produces offsets a younger age than does *Echinopsis* 'Rose 09', contributing to a more balanced plant, with the offsets surrounding the central plant, and with less disparity between size of offsets and size of central plant.

Plants of the new cultivar 'RUBY STARLIGHT' are similar to plants of the pollen parent, in most horticultural characteristics, however, plants of the new cultivar 'RUBY STARLIGHT' differ in the following;

1. *Echinopsis* 'Ruby Starlight' grows faster than the pollen parent *Echinopsis* 'Laser Light', enhancing production times in a commercial nursery.
2. *Echinopsis* 'Ruby Starlight' offsets more profusely than does the pollen parent *Echinopsis* 'Laser Light', enhancing production in the commercial nursery environment.
3. While both *Echinopsis* 'Ruby Starlight' and the pollen parent 'Laser Light' have red flowers, the flower of *Echinopsis* 'Ruby Starlight' is larger than that of *Echinopsis* 'Laser Light'.
4. Due to the fact that *Echinopsis* 'Ruby Starlight' produces more offsets than *Echinopsis* 'Laser Light', the overall morphology of the cluster is more aesthetic than is the cluster of *Echinopsis* 'Laser Light', which produces offsets sparingly, and does not give the effect of a "cluster".

COMMERCIAL COMPARISON

Plants of the new cultivar 'RUBY STARLIGHT' are comparable to the unpatented, commercial variety *Echinopsis* 'Fire Chief'. The two *Echinopsis* varieties are similar in most horticultural characteristics; however, the new variety 'RUBY STARLIGHT' differs in the following:

1. *Echinopsis* 'Ruby Starlight' produces "peanuts" with light areoles, accented by short reddish brown spines, whereas *Echinopsis* 'Fire Chief' produces "peanuts" with fawn colored spines that are much longer in length; contributing to a more "spiny" appearance.
2. *Echinopsis* 'Ruby Starlight' produces larger flowers of ruby red, whereas the flowers of *Echinopsis* 'Fire Chief' are an orange in color.
3 *Echinopsis* 'Ruby Starlight' offsets at a relatively short height, producing a well-balanced cluster, whereas *Echinopsis* 'Fire Chief' produces offsets more towards one side, creating an unbalanced appearing plant, with more disparity between the central stem and the offsets.
4. *Echinopsis* 'Ruby Starlight' produces multiple "flushes" of flowers for a 5 month span, whereas *Echinopsis* 'Fire Chief' blooms on an off for two months, and then rarely produces more flowers before the following spring.

Plants of the new cultivar 'RUBY STARLIGHT' can also be comparable to the unpatented commercial variety *Echinopsis* 'Mephisto'. The two *Echinopsis* varieties are similar in most horticultural characteristics; however, the new variety 'RUBY STARLIGHT' differs in the following:

1. *Echinopsis* 'Ruby Starlight' produces many more offsets than does *Echinopsis* 'Mephisto'.
2. *Echinopsis* 'Ruby Starlight' begins producing offsets at a younger age than does *Echinopsis* 'Mephisto'.
3. *Echinopsis* 'Ruby Starlight' grows much faster than does *Echinopsis* 'Mephisto'.
4. The coloration of the epidermis of *Echinopsis* 'Ruby Starlight' is a much brighter green than the dark brownish green epidermis of the *Echinopsis* 'Mephisto'.
5. *Echinopsis* 'Ruby Starlight' displays ruby red flowers, whereas the flowers of *Echinopsis* 'Mephisto' are tangerine to orange.
6. *Echinopsis* 'Ruby Starlight' produces many more flowers than does *Echinopsis* 'Mephisto', and thereby is a desireable subject for floriculture.

BRIEF DESCRIPTION OF THE PHOTOGRAPHS

The accompanying photographs illustrate in full color typical of plants of *Echinopsis* 'Ruby Starlight' grown in a greenhouse in Vista, Calif. Age of the plant photographed is approximately 5 months from a vegetative offset, "peanut". The photographs were taken using conventional techniques and although colors may appear different from actual colors due to light reflectance it is as accurate as possible by conventional photographic techniques. All photographs provided by the breeder.

DETAILED BOTANICAL DESCRIPTION

Figure 1:
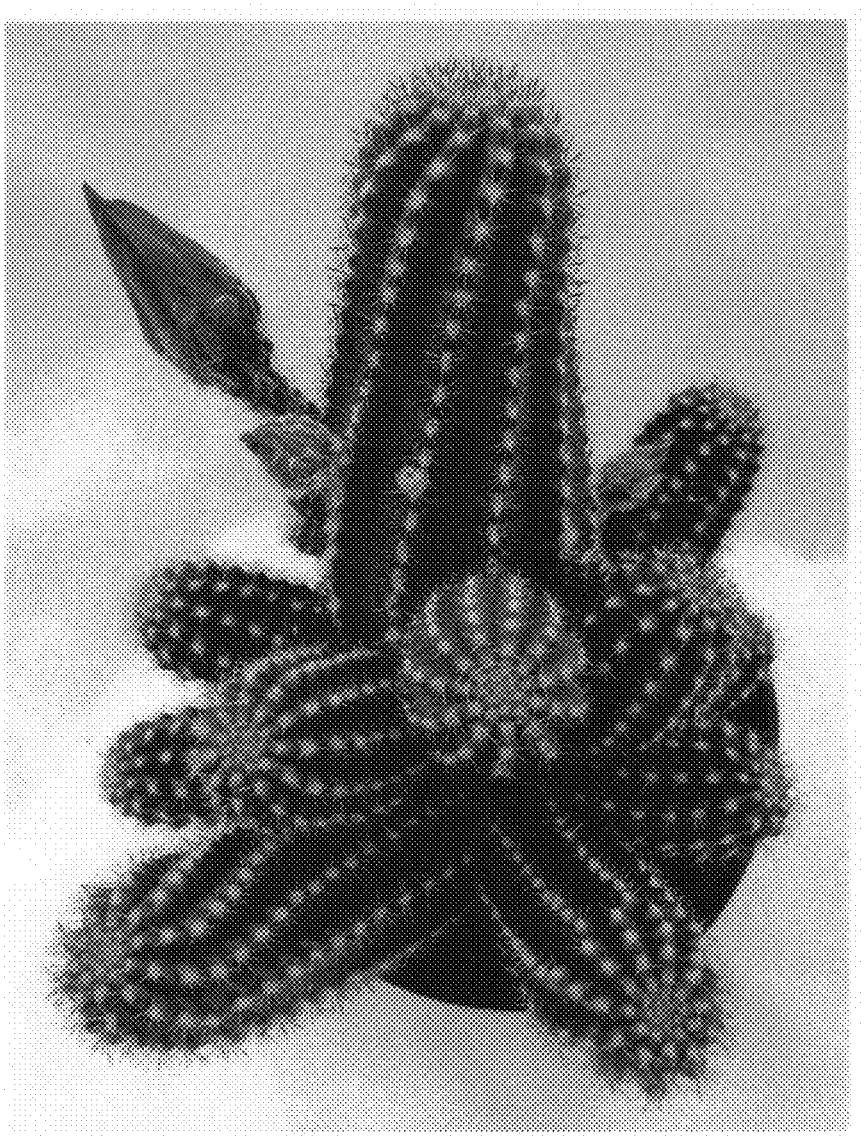
FIG. 1 illustrates in full color the plant morphology of *Echinopsis* hybrid 'Ruby Starlight', grown in a greenhouse (approximately 3000 to 4000 foot candles) in Vista, Calif.
Figure 2:
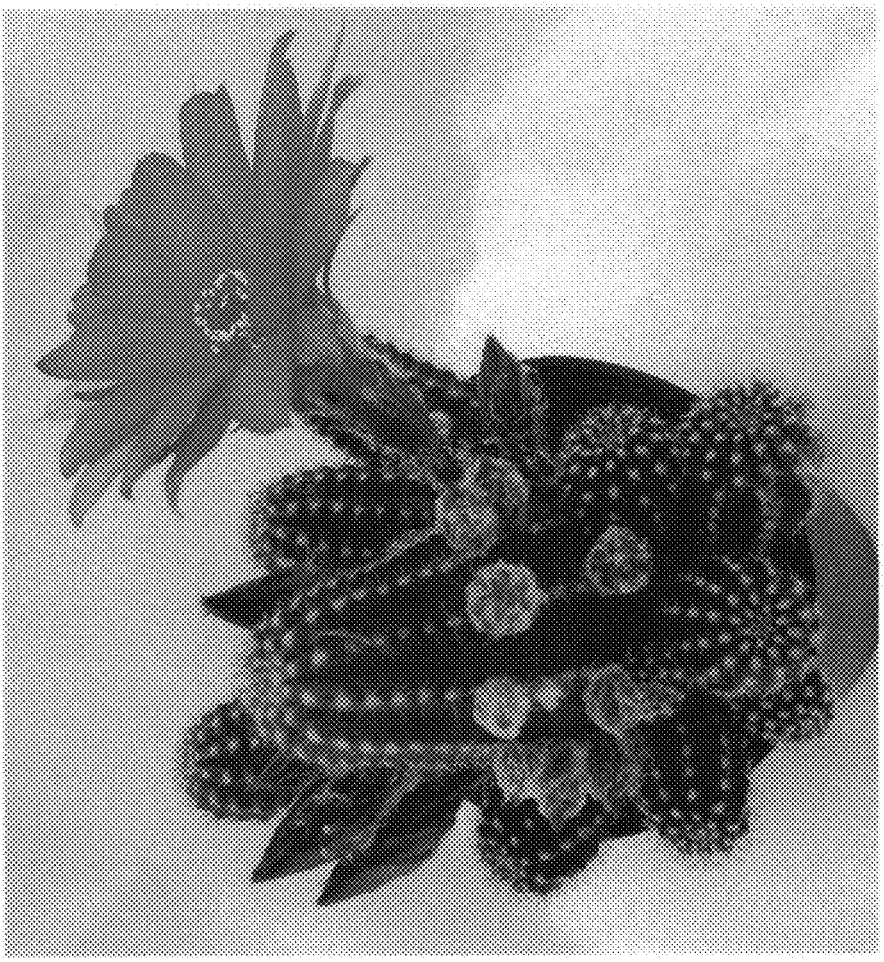
FIG. 2 illustrates in full color *Echinopsis* hybrid 'Ruby Starlight' in an 8 cm pot with an open flower.
Figure 3:
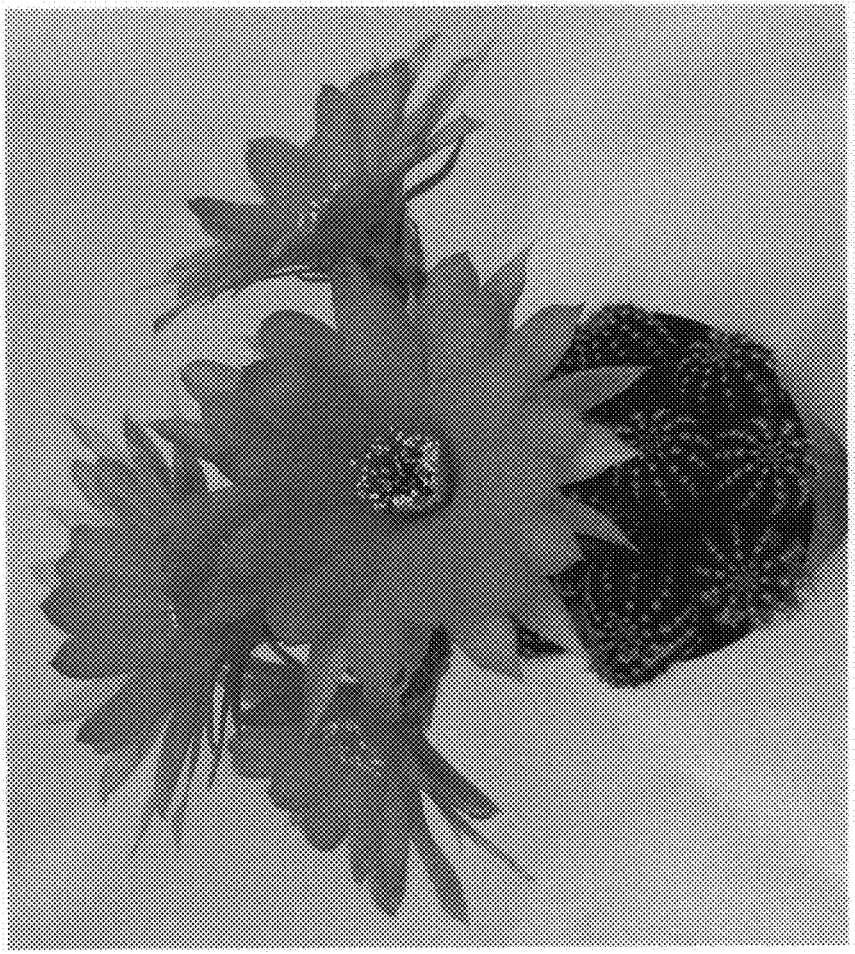
FIG. 3 illustrates in full color *Echinopsis* hybrid 'Ruby Starlight' in an 8 cm pot with multiple open flowers.

In the following description, color references are made to The Royal Horticultural Society Colour Chart, 2007, except where general terms of ordinary dictionary significance are used. The following observations and measurements describe 'Ruby Starlight' plants in a commercial shadehouse in Vista, Calif. Temperatures ranged from 34° F. to 90° F. night and day. No artificial light, photoperiodic treatments or chemical treatments were given to the plants. Natural light conditions were approximately 2500-4000 foot candles of light. Measurements and numerical values represent averages of typical plant types.

Botanical classification: *Echinopsis hybrida* 'RUBY STARLIGHT'.

PROPAGATION

Type of propagation typically used: Vegetative offsets known as "peanuts".

Time to initiate roots: About 3 weeks at approximately 22° to 26° C.

Root description: Densely fibrous.

PLANT

Age of plant described: Approximately 4 months.

Container size of the plant described: 8 cm.

General plant description: Columnar, clump forming small cactus.

Growth habit: Upright. Abundant offsets forming clumps from base.

Plant height: Approximately 9 to 17 cm.

Quantity of offsets: 10 present on a 8 cm pot, during June.

Stem description:

*Diameter*.—Typical range 2.5 to 4.0 cm.

*Length*.—4 to 10 cm.

*Color*.—Near RHS Green 137A.

Areole:

*Spacing*.—Approximately 8 to 10 mm apart on rib.

*Quantity*.—Approximately 150 to 200 per mature stem.

Spine/glochid description:

*Arrangement*.—Spines radially arranged. Average 10 ribs of spines vertically linear, straight to nearly straight. Ribs spaced approximately 8 to 10 mm apart. No prominent central spine, 8 to 10 per aerole. Radial spines approximately 3 mm, colored near Greyed-Orange 165B, 165A at apex. Scant quantity of dense trichomes approximately 1 mm colored near Orange-White 159A.

FLOWER

Natural flowering season: Approximately March through July, occurring in flushes, in Southern California.

Inflorescence type and habit: Open funnel form. Radial flower of multiple whorls.

Flower longevity on plant: 1 to 2 days.

Quantity of flowers: 8 cm pot has approximately 1 to 3 open flowers and 3 to 12 buds.

Individual flower size:

*Diameter*.—Average 5.5 cm.

*Length*.—6.0 cm from base of tube to uppermost petal.

*Flower tube length*.—4.5 to 5.0 cm.

*Flower tube diameter at distal end*.—1.5 cm.

*Flower tube diameter at proximal end*.—0.9 cm.

Petals:

*Petal arrangement*.—Triple whorl.

*Length*.—Average range 2.0 to 3.0 cm.

*Width*.—0.9 cm.

*Quantity*.—Typically 20 to 25.

*Shape*.—Oblong.

*Texture*.—Glabrous all surfaces.

*Appearance*.—Shiny upper surface, moderately shiny lower surface.

*Margin*.—Entire.

*Tip shape*.—Mucronate.

Color:

*Petals*.—When opening: Upper surface: A color between Red-Purple 60A and Red 46A. Lower surface: Near RHS Red 46A. Fully opened: Upper surface: Between Red 46A and Red 53A. Lower Surface: Between Red 46A and Red 53A. Fading. Upper Surface: Near Red 46A. Lower Surface: Near Red 46A.

Flower tube:

*Inner surface*.—Near RHS Red 53B.

*Outer surface*.—Near RHS Greyed-Orange N170D, flushed Red 53C.

Bud:

*Shape*.—Oblong.

*Length*.—Approximate range 1.5 to 4.0 cm, depending on maturity.

*Diameter*.—Approximately 1.5 cm.

*Color*.—Near RHS Green 138B, upper section Red 53A, 53B and 53C.

Peduncle:

*Length*.—1.0 cm.

*Diameter*.—1.0 cm.

*Color*.—Near RHS Greyed-Purple N186B.

*Orientation*.—Approximately 15 to 45° from stem.

*Strength*.—Very strong.

*Texture*.—Villous, moderately dense.

Sepals:

*Shape*.—Quantity per flower: Average range 10 to 16, some not well formed, fused to outer floral tube.

*Length*.—Shortest: Average 1.1 cm longest: 2.5 cm.

*Width*.—Approximately 0.5 cm.

*Shape*.—Linear.

*Margin*.—Entire.

*Apex*.—Acute.

*Texture*.—Glabrous and shiny all surfaces.

*Color, upper surface*.—Near Red 51B.

*Color lower surfaces*.—Near Red 51C, margin 51A.

REPRODUCTIVE ORGANS

Stamens:

*Number*.—Average range 150 to 200.

*Filament length*.—Average range 0.9 to 2.0 cm.

*Filament color*.—Near RHS Red 53A.

Anthers:

*Shape*.—Oblong.

*Length*.—Approximately 2 mm.

*Color*.—Near RHS Orange-White 159A.

*Pollen*.—Color: Near RHS Yellow 9A. Quantity: Moderate.

Pistil:

*Number*.—1.

*Length*.—Approximately 4.5 cm.

*Style*.—Length: Approximately 3.1 cm. Color: Near RHS Red 48A, base of style near Yellow-Green 151D.

*Stigma*.—Shape: 6-parted, each section linear and slightly undulate. Size: Each linear section 4 to 6 mm long, 2 mm wide. Color: Near RHS Green-Yellow 1C.

*Ovary*.—Size: 6 mm long, 4 mm wide. Shape: Narrow oblong. Texture: Sericeous, sticky. Color: Near RHS Yellow-Green 145C.

OTHER CHARACTERISTICS

Fruits and seeds: Seed pods ovate, average range 1.0 to 1.5 cm in length, about 5 mm in diameter. Colored near Grey-brown N199A, densely sericeous, hairs near White 155A. Low to moderate seed production, seeds colored near Greyed-Orange 177C.

Temperature tolerance: USDA zones 10 and above.

Disease/pest resistance:) Neither resistance nor susceptibility to common pathogens or pests of *Echinopsis* observed.

Drought tolerance: Extreme tolerance for drought.

What is claimed is:

1. A new and distinct cultivar of *Echinopsis* plant named 'RUBY STARLIGHT' as herein illustrated and described.

* * * * *